(12) United States Patent
Jared

(10) Patent No.: US 6,865,442 B1
(45) Date of Patent: Mar. 8, 2005

(54) METHOD OF PRODUCING ORTHOTIC DEVICE UTILIZING MILL PATH ABOUT PERPENDICULAR AXIS

(76) Inventor: Stephen J. Jared, 405B W. Tularosa, Orange, CA (US) 92866

( * ) Notice: Subject to any disclaimer, the term of this patent is extended or adjusted under 35 U.S.C. 154(b) by 925 days.

(21) Appl. No.: 09/694,900

(22) Filed: Oct. 24, 2000

(51) Int. Cl.$^7$ ............................................. G06F 19/00
(52) U.S. Cl. ..................................................... 700/191
(58) Field of Search ................................. 700/159, 163, 700/164, 166, 172, 176, 184, 187, 191, 78, 117, 118, 160; 408/26, 30, 147, 178, 180, 190, 210, 222; 82/14; 83/116

(56) References Cited

U.S. PATENT DOCUMENTS

| | | | |
|---|---|---|---|
| 4,306,598 A | 12/1981 | Peot | |
| 4,454,618 A | 6/1984 | Curchod | |
| 4,651,599 A * | 3/1987 | Ley ................................. | 82/18 |
| 4,686,993 A | 8/1987 | Grumbine | |
| 5,054,148 A * | 10/1991 | Grumbine .................. | 12/142 N |
| 5,087,159 A * | 2/1992 | Thomas ....................... | 409/132 |
| 5,432,703 A | 7/1995 | Clynch et al. .............. | 700/163 |
| 5,449,256 A * | 9/1995 | Sundman ..................... | 409/134 |
| 5,687,467 A | 11/1997 | Bergmann et al. | |
| 5,746,952 A | 5/1998 | Marshall | |
| 5,800,364 A | 9/1998 | Glennie et al. ............. | 600/592 |
| 6,142,965 A | 11/2000 | Mathewson ................... | 602/62 |
| 6,267,594 B1 * | 7/2001 | Hugo .......................... | 433/119 |
| 6,447,223 B1 * | 9/2002 | Farah et al. ................. | 409/132 |

OTHER PUBLICATIONS

Hemmett et al. "A Robust and Efficient Approach to Feedrate Selection fo 3-axis Machining" 2000, ASME IMECE.*

* cited by examiner

Primary Examiner—Leo Picard
Assistant Examiner—Chad Rapp
(74) Attorney, Agent, or Firm—Stetina Brunda Garred & Brucker

(57) ABSTRACT

In accordance with the present invention, there is provided a method of milling an orthotic device by using a computer controlled milling tool. The orthotic device is defined by a orthotic device upper contour. The method begins with providing a workpiece which defines a mill plane and a perpendicular axis thereto. The method further provides for milling the milling tool into the workpiece along the perpendicular axis to a depth corresponding to the orthotic device upper contour. The method further provides for translating the milling tool relative to the workpiece in the mill plane along a milling path while adjusting the depth of the milling tool to correspond to the orthotic device upper contour to selectively remove material from the workpiece for producing the orthotic device therefrom. The milling path is characterized by a plurality of mill rotations about the perpendicular axis. Successive ones of the mill rotations are radially further from the perpendicular axis.

30 Claims, 4 Drawing Sheets

METHOD OF PRODUCING ORTHOTIC DEVICE UTILIZING MILL PATH ABOUT PERPENDICULAR AXIS

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention relates generally to fabrication of orthotic devices, and more particularly to a method of producing orthotic devices utilizing an optimized milling path.

The prior art provides for the computer controlled manufacturing of orthotic devices or appliances from a workpiece of solid material, such as plastic. Typically, such a process begins with the generation of computer model of a patient's foot, for example. This may be accomplished by using an optical scanner or electro-mechanical contact apparatus. The computer model may be adapted with a prescriptive modification to generate computer model of a desired orthotic device. A milling tool may be used to selectively remove material from the plastic workpiece so as to expose a surface contour corresponding to the desired orthotic device computer model. Thus, the remaining material of the workpiece forms the basis of the desired orthotic device. This may be accomplished via a computer numerical controlled (CNC) process. Subsequent to such CNC process further machining may be required for final completion of the device. For example, a surface machining process may be desired, such as grinding, polishing or sandblasting.

For example, a prior art milling path is disclosed in U.S. Pat. No. 5,054,148 which as understood calls for the milling tool to translate in a back and forth motion across the desired orthotic device to form a series of parallel grooves. However, such a prior art milling path requires abrupt direction changes, 180 degree turns. Such abrupt direction changes require that the associated milling tool decelerate upon making such abrupt direction changes and may even result in a momentary stoppage of motion. Subsequently, the milling tool is required to quickly accelerate to continue milling. Such deceleration and acceleration cycling is inefficient in terms of overall fabrication time of the orthotic device.

It is therefore evident that there exists a need in the art for a method of more efficiently producing orthotic devices in comparison to the prior art.

BRIEF SUMMARY OF THE INVENTION

In accordance with an aspect of the present invention, there is provided a method of milling an orthotic device by using a computer controlled milling tool. The orthotic device is defined by an orthotic device upper contour. The method begins with providing a workpiece which defines a mill plane and a perpendicular axis thereto. The method further provides for milling the milling tool into the workpiece along the perpendicular axis to a depth corresponding to the orthotic device upper contour. The method further provides for translating the milling tool relative to the workpiece in the mill plane along a milling path while adjusting the depth of the milling tool to correspond to the orthotic device upper contour to selectively remove material from the workpiece for producing the orthotic device therefrom. The milling path is characterized by a plurality of mill rotations about the perpendicular axis. Successive ones of the mill rotations are radially further from the perpendicular axis.

Preferably, the milling tool is translated in the mill plane at a substantially constant speed. Further, the milling tool is sized and configured to perform a climb cut into the workpiece. The milling tool has a spherical-shaped end mill and the milling tool is translated along the milling path which aligns the spherical-shaped end mill tangentially with the orthotic device upper contour.

In another embodiment of an aspect of the present invention, there is a method of generating data for controlling a computer controlled milling tool to mill a workpiece to form an orthotic device therefrom having an orthotic device upper contour. The method provides for accessing contour data representative of the orthotic device upper contour. The contour data is relatable to a mill plane and a perpendicular axis thereto. The method further provides for generating milling path data using the accessed contour data. The milling path data is representative of a milling path characterized by a plurality of mill rotations about the perpendicular axis. Successive ones of the mill rotations are radially further from the perpendicular axis. Preferably, the milling path data is calculated to translate the milling tool in the mill plane at a substantially constant speed. Further, the milling path data is calculated to configure the milling tool to perform a climb cut into the workpiece. The milling tool may have a spherical-shaped end mill and the milling path is calculated to align the spherical-shaped end mill tangentially with the orthotic device upper contour.

In another embodiment of an aspect of the present invention, there is provided a method of milling an orthotic device by using a computer controlled milling tool. The milling tool has a spherical-shaped end mill. The orthotic device is defined by an orthotic device upper contour. The method begins with providing a workpiece defining a mill plane and a perpendicular axis thereto. The method further provides for milling the milling tool into the workpiece along the perpendicular axis to a depth corresponding to the orthotic device upper contour. The method further provides for translating the milling tool relative to the workpiece in the mill plane along a milling path while adjusting the depth of the milling tool to correspond to the orthotic device upper contour to selectively remove material from the workpiece for producing the orthotic device therefrom. The milling path is configured to align the spherical-shaped end mill tangentially with the orthotic device upper contour. Preferably, the milling path being characterized by a plurality of mill rotations about the perpendicular axis. Successive ones of the mill rotations are radially further from the perpendicular axis. The milling tool is translated in the mill plane at a substantially constant speed.

In yet another embodiment of an aspect of the present invention, there is a method of generating data for controlling a computer controlled milling tool to mill a workpiece to form an orthotic device therefrom having an orthotic device upper contour. The milling tool has a spherical-shaped end mill. The method provides for accessing contour data representative of the orthotic device upper contour. The contour data is relatable to a mill plane and a perpendicular axis thereto. The method further provides for generating milling path data using the accessed contour data. The milling path data is representative of a milling path. The milling path is configured to align the spherical-shaped end mill tangentially with the orthotic device upper contour. Preferably, the milling path is characterized by a plurality of mill rotations about the perpendicular axis. Successive ones of the mill rotations are radially further from the perpendicular axis. The milling tool is translated in the mill plane at a substantially constant speed.

As such, the present invention mitigates the inefficiencies and limitations associated with prior art methods of producing orthotic devices. Advantageously, the present invention utilizes a milling path which seeks to optimize the time, power and motion efficiency of the milling tool. In this regard, in the preferred embodiment of the present invention, the milling path is characterized by a plurality of mill rotations about the perpendicular axis with successive ones of the mill rotations being radially further from the perpendicular axis. Such a milling path is contemplated to avoid or mitigate the need to perform abrupt direction changes or highly radiused turns. Such abrupt direction changes or highly radiused turns typically require that the associated milling tool decelerate upon making such abrupt direction changes and may even result in a momentary stoppage of motion, as in the case of a complete 180 degree direction change. Subsequently, the milling tool is required to quickly accelerate to continue milling. The present invention mitigates against such deceleration and acceleration cycling, thereby allowing milling to take place at a substantially constant rate in comparison to the prior art. This advantageously translates into a reduced overall fabrication time of the orthotic device.

Further, such a milling path facilitates the milling tool to perform a climb cut into the workpiece. Significantly, a climb cut tends to draw the material desired to be milled towards the milling tool. This tends to result in less power consumption requirements of the milling tool. In contrast, prior art milling paths tend to employ both climb cuts and the less efficient conventional cuts.

Another advantage of an aspect of the present invention is in the case where the milling tool has a spherical-shaped end mill and the milling tool is translated along the milling path which aligns the spherical-shaped end mill tangentially with the orthotic device upper contour. In this regard, the milling path of the present invention compensates for a tool center off-set between an optimized milling contact point upon the spherical-shaped end mill and the material being milled. In particular, the tangent of the spherical-shaped end mill to the material being milled of the workpiece is used to calculate the milling path. This is especially significant adjacent highly contoured portions of the orthotic device such at a posterior portion thereof, such as corresponding to a heel portion of the orthotic device.

Accordingly, the present invention represents a significant advance in the art.

BRIEF DESCRIPTION OF THE SEVERAL VIEWS OF THE DRAWING

These, as well as other features of the present invention, will become more apparent upon reference to the drawings wherein.

DETAILED DESCRIPTION OF THE INVENTION

Figure 1:
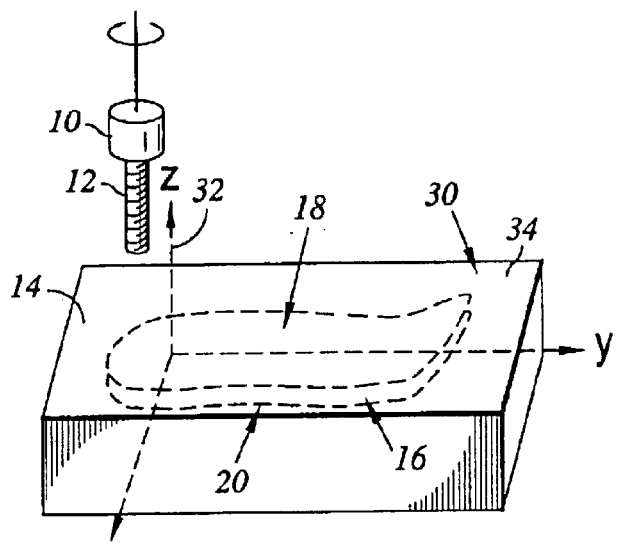
FIG. 1 is a symbolic perspective view of a milling tool as shown with a workpiece.

Referring now to the drawings wherein the showings are for purposes of illustrating a preferred embodiment of the present invention only, and not for purposes of limiting the same, FIGS. 1–10 illustrate the method of producing orthotic devices of the present invention.

Referring now to FIG. 1, the present invention contemplates use of a milling tool 10 as symbolically depicted. The milling tool 10 is computer controlled, and may be a computer numeric controlled (CNC) device. The milling tool 10 is equipped with an end mill 12. Preferably, the end mill 12 is spherical-shaped. The milling tool 10 is configured to move the end mill 12 relative to a workpiece 14. The milling tool 10 and supporting equipment for moving the workpiece 12 relative thereto, such servo motors, may be chosen from those which is well known to one of ordinary skill in the art.

The present invention contemplates the milling of a workpiece 14 to form an orthotic device 16 therefrom (as symbolically shown in phantom). Suitable materials used to form the workpiece 14 may be chosen from those well known to one of ordinary skill in the art. As used herein it is contemplated that the term orthotic device 16 may include any device which is configured to be affixed adjacent a distal end of an anatomical structure, such as the bottom of a patient's foot. Additionally, it is contemplated that the term orthotic device 16 further includes positive moldings of such anatomical structure distal end, corrected or uncorrected. In a preferred embodiment of an aspect of the present invention, the orthotic device 16 has orthotic device upper and lower contours 18, 20.

The method begins with providing the workpiece 14. As the typical orthotic device 16 is contemplated to be contained within a rectangular solid volume, the workpiece 14 will typically be similarly shaped. It is contemplated that multiple workpieces 14 each associated with an orthotic device 16 may be formed from a single block of material. In this regard, the term workpiece 14 as used herein may refer to a portion of a material dedicated to the formation of an orthotic device 16.

The workpiece 14 defines a mill plane 30 (Z-axis) and a perpendicular axis 32 (the plane defined by the X-axis and the Y-axis) thereto. In this regard, the workpiece 14 may have a workpiece top surface 34. It is contemplated that movement of the milling tool 10 relative to the workpiece 14 may be accomplished any number of ways. For example, a conventional milling technique involves the milling tool 10 having a degree of freedom along a vertical or Z-axis which is perpendicular to the workpiece top surface 34, and the workpiece 14 having degrees of freedom in a plane perpendicular to such vertical axis. In this regard, the milling tool 10 may be configured to move along the perpendicular axis 32 and the workpiece 14 may be configured to translate in the mill plane 30. As such, as contemplated herein, movement of the milling tool 10 with respect to the workpiece 14 is in regards to relative movement.

Figure 2:
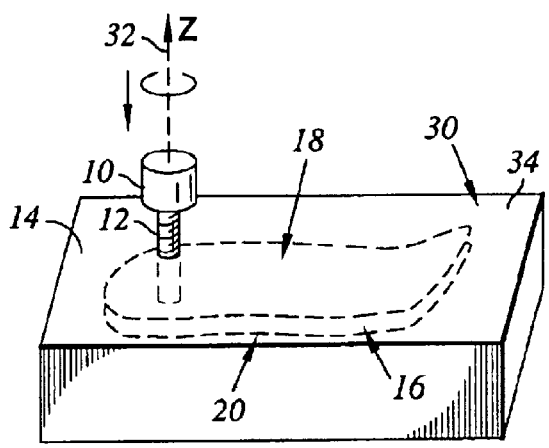
FIG. 2 is the milling tool and workpiece of FIG. 1 as shown with the milling tool disposed along a perpendicular axis into the workpiece to a depth of an orthotic device upper contour.

Referring now to FIG. 2, the method further provides for milling the milling tool 10 into the workpiece 14 along the perpendicular axis 32 to a depth corresponding to the orthotic device upper contour 18.

Figure 3:
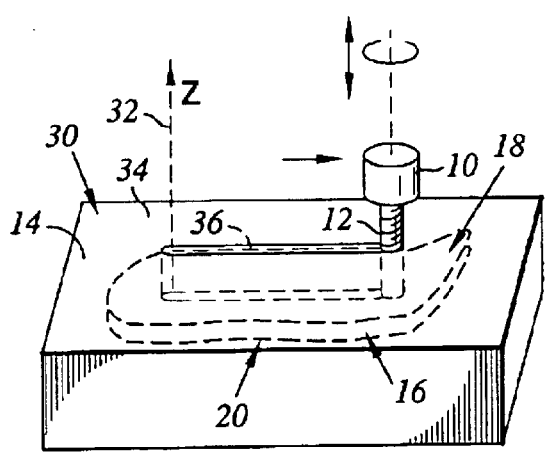
FIG. 3 is the milling tool and workpiece of 3 Figure as shown with the milling tool translated along a milling path.
Figure 4:
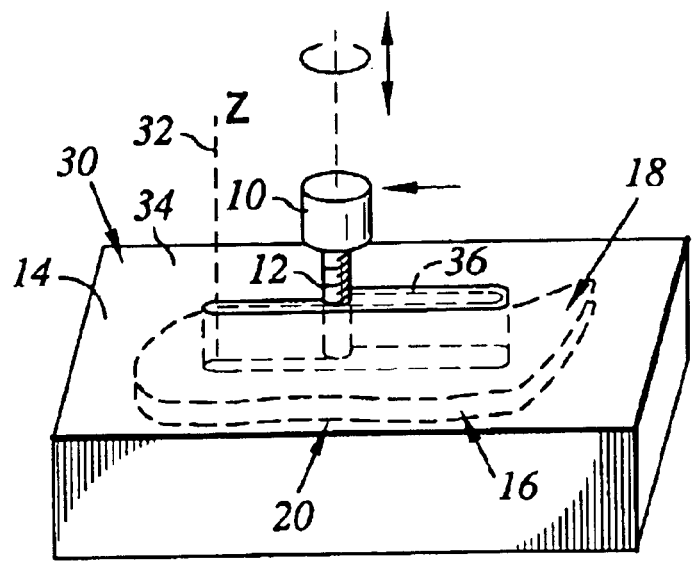
FIG. 4 is the milling tool and workpiece of FIG. 3 as shown with the milling tool translated along the milling path about the perpendicular axis.
Figure 5:
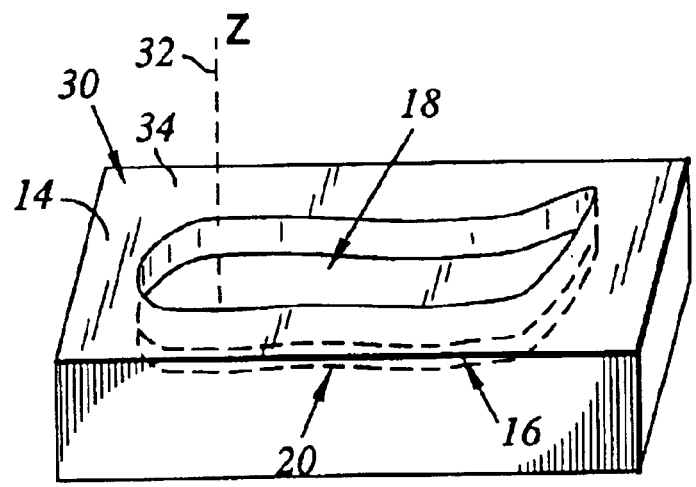
FIG. 5 is the workpiece of FIG. 4 as shown with an exposed orthotic device upper contour.

The method further provides for translating the milling tool 10 relative to the workpiece 14 in the mill plane 30 along a milling path 36 while adjusting the depth of the milling tool 10 to correspond to the orthotic device upper contour 18 to selectively remove material from the workpiece 14 for producing the orthotic device 16 therefrom. In sequence with FIG. 2, FIG. 3 depicts the milling tool 10 having translated along the Y-axis along the milling path 36 generally away from the Z-axis. In sequence with FIG. 3, FIG. 4 depicts the milling tool 10 having continued along the milling path 36 generally towards the Z-axis.

As used herein, the milling path 36 may include a path which refers to a locus of points which is associated with fixed portion of the milling tool 10, such as a center of an end mill or the distal-most point thereof, during a milling operation. However, in another embodiment of an aspect of the present invention, as further discussed below, the milling path 36 may be generated to account for such locus of points which is associated with a point of contact between the milling tool 10 and the intended orthotic device upper contour 18 (or intended orthotic device lower contour 20, as applicable) during a milling operation.

Figure 6:
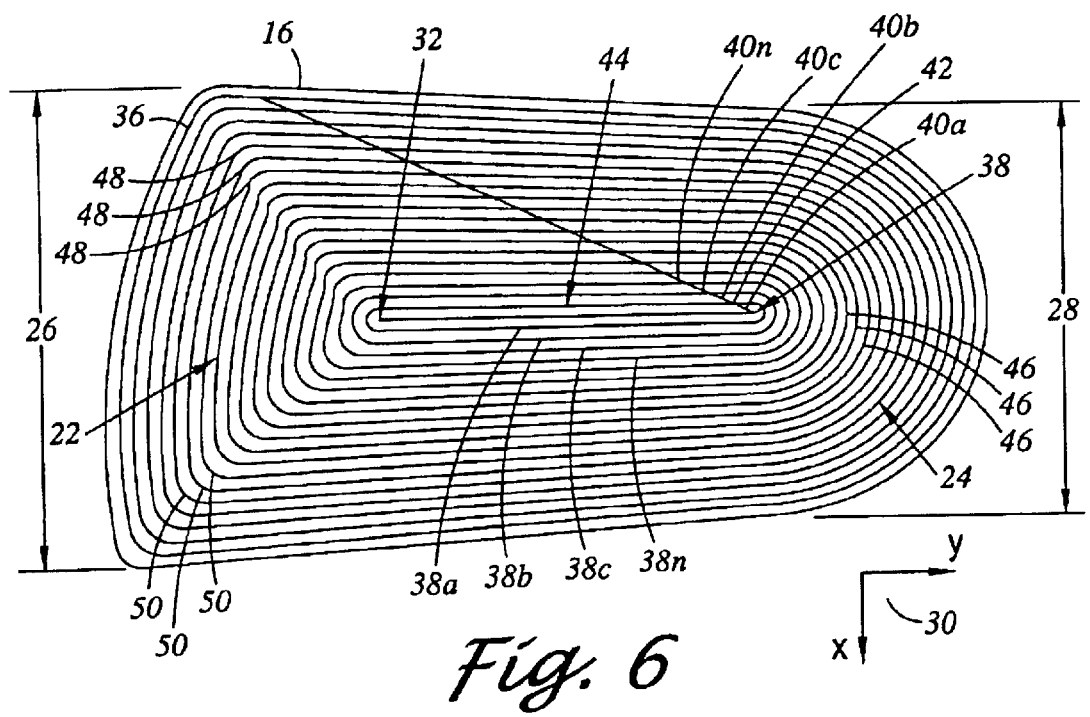
FIG. 6 is a top view of a milling path of the method of the present invention.
Figure 7:
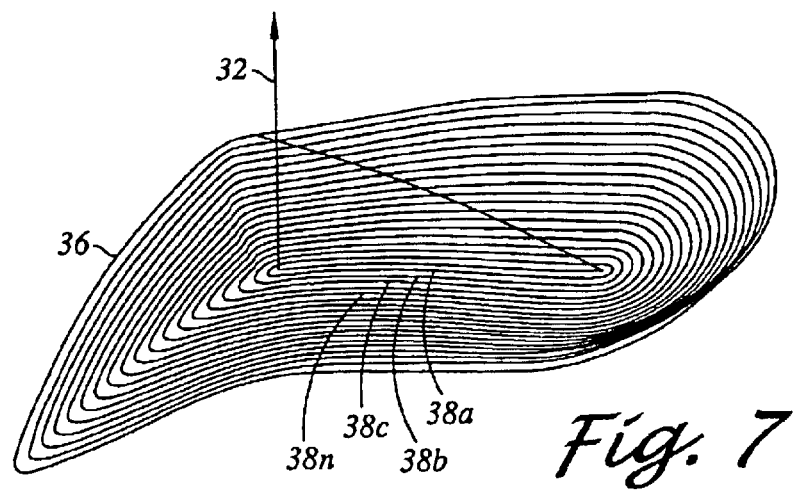
FIG. 7 is a perspective view of the milling path of FIG. 6.

Referring now to FIG. 6, there is depicted a top view of the milling path 36 as superimposed upon the orthotic device 16 along the orthotic device upper contour 18. FIG. 7 is a perspective view of milling path 36 only.

Referring to FIG. 6, the milling tool 10 of FIG. 3 corresponds to milling path location 38. As such, in this embodiment, the milling tool 10 translates from the perpendicular axis 32 to milling path location 38. Next, the milling path 36 continues along a lane change segment 40a to milling path location 42. From milling path location 42 the milling path 36 continues generally towards the perpendicular axis 32 through milling path location 44 which corresponds to position of the milling tool 10 of FIG. 4.

Importantly, in the present embodiment of the present invention, the milling path 36 is characterized by a plurality of mill rotations 38n about the perpendicular axis 32. Successive ones of the mill rotations 38n, such as mill rotations 38a, 38b and 38c, are radially further from the perpendicular axis 32. As used herein the terms radially further refers to the overall dimensions of the mill rotations 38n in comparison with each other. In this regard, milling path location 44 is located upon mill rotation 38a. The next successive one of the mill rotations 38n is mill rotation 38b. Lane change segment 40b is utilized to traverse from mill rotation 38b to mill rotation 38c. Similarly, lane change segment 40c is utilized to traverse outwardly from mill rotation 38c to the next succeeding mill rotations 38n. Other lane change segments 40n are utilized in similar fashion.

While the mill rotations 38n are depicted to be connected via the use of the lane change segments 40n, such lane change segments 40n are not so required. In this regard, it is contemplated that the mill rotations 38n may be successively joined by a gradual spiraling of the milling rotations 38n such that an end of a given one blends with the beginning of the next.

The mill rotations 38 are generally elliptical-shaped. In this regard, as used herein, the term "generally elliptical-shaped" not only refers to circles and ellipses, but more loosely refers to generally rounded polygonal shapes as well.

In a typical arrangement, the orthotic device 16 has opposing anterior and posterior portions 22, 24. The anterior portion 22 has a primary width 26 and the posterior portion 24 has a secondary width 28. Typically, the orthotic device 16 has a primary width 26 greater than the secondary width 28, as shown. In the case of the orthotic device 16 being used in connection with a patient's foot, the posterior portion 24 would correspond to the heel of the foot. In this regard, the portion of the orthotic device upper contour 18 which is disposed adjacent the posterior portion 24 would be anticipated to be substantially contoured. The present embodiment of the method of the present invention will now be more fully discussed in the context of such typical, but not required, orthotic device configuration.

In an embodiment of the present invention, given ones of a portion of the mill rotations 38n are characterized by having an elliptical section 46 (a representative few are denoted) adjacent the posterior portion 24.

In an embodiment of the present invention, given ones of the portion of the mill rotations 38n are characterized by having a first arced section 48 (a representative few are denoted) and a second arced section 50 (a representative few are denoted) disposed adjacent the anterior portion 22.

In the preferred embodiment of the present invention, the milling tool 10 is translated in the mill plane 30 at a substantially constant speed. In this regard, the minimal radius of arcs and turns along the milling path 36 are preferably calculated to maintain such constant speed of translation. It is contemplated that such minimal radius is a function of the various tolerances of the movement control mechanisms, e.g., bearings and ball screws.

Advantageously, in the preferred embodiment of the present invention, the milling tool 10 is sized and configured to perform a climb cut into the workpiece 14. In this regard, in the embodiment shown, the milling tool 10 is rotated clockwise with the milling path 36 following milling rotations 38n counter-clockwise.

Figure 8:
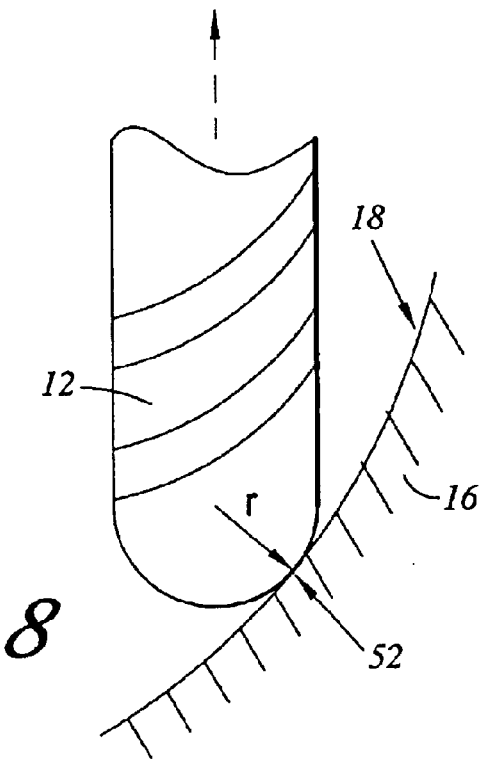
FIG. 8 is a symbolic sectional side view of an end mill of a milling tool in relation to the orthotic device upper contour.

Referring now to FIG. 8 there is depicted a symbolic sectional side view of the end mill 12 of the milling tool 10 in relation to the orthotic device upper contour 18. In another embodiment of an aspect of the present invention, the milling tool 10 has a spherical-shaped end mill 12. In this regard, the end mill 12 may be characterized by a radius r. The milling tool 10 may be translated along the milling path 36 which aligns the spherical-shaped end mill 12 tangentially with the orthotic device upper contour 18. In this respect, the end mill 12 contacts the upper device contour 18 at tangent point 52. It is contemplated such tangential milling in reference to the intended contour compensates for an off-set between a fixed reference point of the end mill 12, such as along its axis. Thus, the mill path 36 is a function of the upper contour 18 (in three dimensions), rather than the perimeter boundaries of the orthotic device in the mill plane 30. In this regard, because the milling path 36 takes into account such offset, such milling path 36 is contemplated to result in an actually milled contour which is more closely manufactured to its intended design.

It is contemplated that the above described milling operation and techniques as discussed and shown in reference to the orthotic device upper contour 18 may be similarly applied to the orthotic device lower contour 20.

Figure 9:
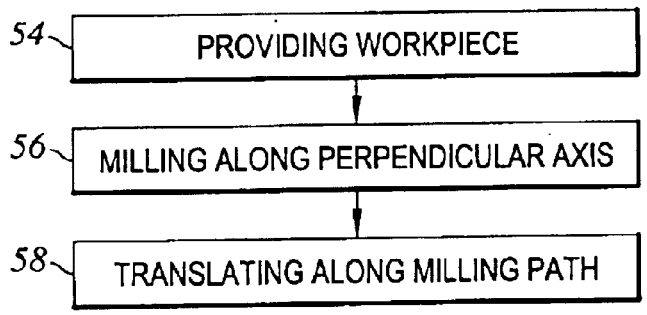
FIG. 9 is a flow diagram of a method of an embodiment of an aspect of the present invention.

Referring now to FIG. 9, there is depicted a flow diagram of a method of an embodiment of an aspect of the present invention as discussed above. In this regard, the method generally calls for the steps of providing 54 the work piece 14, milling 56 along the perpendicular axis 32, and translating 58 along the milling path 36.

Figure 10:
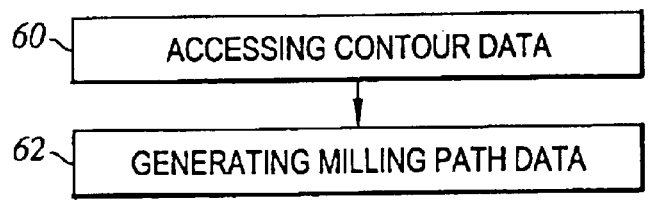
FIG. 10 is a flow diagram of a method of another embodiment of an aspect of the present invention.

Referring now to FIG. 10, the present invention further contemplates a method of generating data for controlling the computer controlled milling tool 10 to mill the workpiece 14 to form the orthotic device 16 therefrom having the orthotic device upper contour 18. In this respect, such method is contemplated to be performed within a computer executable software program which may be self contained, such a discrete software module, or distributed between multiple software components.

The method initially contemplates accessing 60 contour data representative of the orthotic device upper contour 18. The contour data is relatable to the mill plane 30 and the perpendicular axis 32 thereto. In this regard, such data is contemplated to be stored in a computer readable format. Next, milling path data is generated 62 using the accessed contour data. The milling path data is representative of a milling path (depicted as milling path 36) characterized by a plurality of mill rotations (depicted as mill rotations 38$n$) about the perpendicular axis 36. Successive ones of the mill rotations 38$n$ being radially further from the perpendicular axis 36.

Additional modifications and improvements of the present invention may also be apparent to those of ordinary skill in the art. Thus, the particular combination of method step and/or parts described and illustrated herein is intended to represent only one embodiment of the present invention, and is not intended to serve as limitations of alternative method and/or devices within the spirit and scope of the invention.

What is claimed is:

1. A method of milling an orthotic device by using a computer controlled milling tool, the orthotic device defined by a orthotic device upper contour, the orthotic device having opposing anterior and posterior portions thereof, the method comprising the steps of:
   a) providing a workpiece defining a mill plane and a perpendicular axis thereto;
   b) milling the milling tool into the workpiece along the perpendicular axis to a depth corresponding to the orthotic device upper contour; and
   c) translating the milling tool relative to the workpiece in the mill plane along a milling path while adjusting the depth of the milling tool to correspond to the orthotic device upper contour to selectively remove material from the workpiece for producing the orthotic device therefrom, the milling path being characterized by a plurality of mill rotations about the perpendicular axis, successive ones of the mill rotations being radially further from the perpendicular axis, given ones of a portion of the mill rotations each having an elliptical section adjacent the posterior portion.

2. The method of claim 1 wherein step c) the milling tool is translated in the mill plane at a substantially constant speed.

3. The method of claim 1 wherein step c) the milling tool is sized and configured to perform a climb cut into the workpiece.

4. The method of claim 1 wherein the milling tool has a spherical-shaped end mill and wherein step c) the milling tool is translated along the milling path which aligns the spherical-shaped end mill tangentially with the orthotic device upper contour.

5. The method of claim 1 wherein the mill rotations each include at least one elliptical section thereof.

6. The method of claim 5 wherein the mill rotations are generally elliptical-shaped.

7. The method of claim 1 wherein the given ones of the portion of the mill rotations each have a first arced section and a second arced section disposed adjacent the anterior portion.

8. The method of claim 1 wherein the orthotic device has opposing anterior and posterior portions thereof, the anterior portion has a primary width and the posterior portion has a secondary width, the primary width is greater than the secondary width.

9. The method of claim 8 wherein given ones of a portion of the mill rotations each have an elliptical section disposed adjacent the posterior portion.

10. The method of claim 9 wherein the given ones of the portion of the mill rotations each have a first arced section and a second arced section disposed adjacent the anterior portion.

11. A method of generating data for controlling a computer controlled milling tool to mill a workpiece to form an orthotic device therefrom having an orthotic device upper contour, the orthotic device having opposing anterior and posterior portions thereof, the method comprising the steps of:
   a) accessing contour data representative of the orthotic device upper contour, the contour data being relatable to a mill plane and a perpendicular axis thereto; and
   b) generating milling path data using the accessed contour data, the milling path data being representative of a milling path characterized by a plurality of mill rotations about the perpendicular axis, successive ones of the mill rotations being radially further from the perpendicular axis, given ones of a portion of the mill rotations each having an elliptical section adjacent the posterior portion.

12. The method of claim 11 wherein the milling path data is calculated to translate the milling tool in the mill plane at a substantially constant speed.

13. The method of claim 11 wherein the milling path data is calculated to configure the milling tool to perform a climb cut into the workpiece.

14. The method of claim 11 wherein the milling tool has a spherical-shaped end mill and wherein step b) the milling path is calculated to align the spherical-shaped end mill tangentially with the orthotic device upper contour.

15. The method of claim 11 wherein the mill rotations each include at least one elliptical section thereof.

16. The method of claim 15 wherein the mill rotations are generally elliptical-shaped.

17. The method of claim 11 wherein the given ones of the portion of the mill rotations each have a first arced section and a second arced section disposed adjacent the anterior portion.

18. The method of claim 11 wherein the orthotic device has opposing anterior and posterior portions thereof, the anterior portion has a primary width and the posterior portion has a secondary width, the primary width is greater than the secondary width.

19. The method of claim 18 wherein given ones of a portion of the mill rotations each have an elliptical section disposed adjacent the posterior portion.

20. The method of claim 19 wherein the given ones of the portion of the mill rotations each have a first arced section and a second arced section disposed adjacent the anterior portion.

21. A method of milling an orthotic device by using a computer controlled milling tool, the milling tool having a spherical-shaped end mill, the orthotic device defined by a orthotic device upper contour, the orthotic device having opposing anterior and posterior portions thereof, the method comprising the steps of:
   a) providing a workpiece defining a mill plane and a perpendicular axis thereto;
   b) milling the milling tool into the workpiece along the perpendicular axis to a depth corresponding to the orthotic device upper contour; and
   c) translating the milling tool relative to the workpiece in the mill plane along a milling path while adjusting the depth of the milling tool to correspond to the orthotic device upper contour to selectively remove material from the workpiece for producing the orthotic device therefrom, the milling path being configured to align the spherical-shaped end mill tangentially with the orthotic device upper contour, given ones of a portion of the mill rotations each having an elliptical section adjacent the posterior portion.

22. The method of claim 21 wherein the milling path being characterized by a plurality of mill rotations about the perpendicular axis, successive ones of the mill rotations being radially further from the perpendicular axis.

23. The method of claim 21 wherein step c) the milling tool is translated in the mill plane at a substantially constant speed.

24. A method of generating data for controlling a computer controlled milling tool to mill a workpiece to form an orthotic device therefrom having an orthotic device upper contour, the orthotic device has opposing anterior and posterior portions thereof, the milling tool having a spherical-shaped end mill, the method comprising the steps of:
   a) accessing contour data representative of the orthotic device upper contour, the contour data being relatable to a mill plane and a perpendicular axis thereto; and
   b) generating milling path data using the accessed contour data, the milling path data being representative of a milling path, the milling path being configured to align the spherical-shaped end mill tangentially with the orthotic device upper contour, given ones of a portion of the mill rotations each having an elliptical section adjacent the posterior portion.

25. The method of claim 24 wherein the milling path being characterized by a plurality of mill rotations about the perpendicular axis, successive ones of the mill rotations being radially further from the perpendicular axis.

26. The method of claim 24 wherein step b) the milling tool is translated in the mill plane at a substantially constant speed.

27. A method of milling an orthotic device by using a computer controlled milling tool, the orthotic device defined by a orthotic device upper contour, the method comprising the steps of:
   a) providing a workpiece defining a mill plane and a perpendicular axis thereto;
   b) milling the milling tool into the workpiece along the perpendicular axis to a depth corresponding to the orthotic device upper contour; and
   c) translating the milling tool relative to the workpiece in the mill plane along a milling path while adjusting the depth of the milling tool to correspond to the orthotic device upper contour to selectively remove material from the workpiece for producing the orthotic device therefrom, the milling path being characterized by a plurality of mill rotations about the perpendicular axis, successive ones of the mill rotations being radially further from the perpendicular axis, wherein the orthotic device having opposing anterior and posterior portions thereof, the anterior portion having a primary width and the posterior portion having a secondary width, the primary width being greater than the secondary width.

28. A method of generating data for controlling a computer controlled milling tool to mill a workpiece to form an orthotic device therefrom having an orthotic device upper contour, the method comprising the steps of:
   a) accessing contour data representative of the orthotic device upper contour, the contour data being relatable to a mill plane and a perpendicular axis thereto; and
   b) generating milling path data using the accessed contour data, the milling path data being representative of a milling path characterized by a plurality of mill rotations about the perpendicular axis, successive ones of the mill rotations being radially further from the perpendicular axis, wherein the orthotic device having opposing anterior and posterior portions thereof, the anterior portion having a primary width and the posterior portion having a secondary width, the primary width being greater than the secondary width.

29. A method of milling an orthotic device by using a computer controlled milling tool, the milling tool has a spherical-shaped end mill, the orthotic device defined by a orthotic device upper contour, the method comprising the steps of:
   a) providing a workpiece defining a mill plane and a perpendicular axis thereto;
   b) milling the milling tool into the workpiece along the perpendicular axis to a depth corresponding to the orthotic device upper contour; and
   c) translating the milling tool relative to the workpiece in the mill plane along a milling path while adjusting the depth of the milling tool to correspond to the orthotic device upper contour to selectively remove material from the workpiece for producing the orthotic device therefrom, the milling path being configured to align the spherical-shaped end mill tangentially with the orthotic device upper contour, wherein the orthotic device having opposing anterior and posterior portions thereof, the anterior portion having a primary width and the posterior portion having a secondary width, the primary width being greater than the secondary width.

30. A method of generating data for controlling a computer controlled milling tool to mill a workpiece to form an orthotic device therefrom having an orthotic device upper contour, the milling tool has a spherical-shaped end mill, the method comprising the steps of:
   a) accessing contour data representative of the orthotic device upper contour, the contour data being relatable to a mill plane and a perpendicular axis thereto; and
   b) generating milling path data using the accessed contour data, the milling path data being representative of a milling path, the milling path being configured to align the spherical-shaped end mill tangentially with the orthotic device upper contour, wherein the orthotic device having opposing anterior and posterior portions thereof, the anterior portion having a primary width and the posterior portion having a secondary width, the primary width being greater than the secondary width.

* * * * *